US006812477B2

(12) United States Patent
Matsunami

(10) Patent No.: US 6,812,477 B2
(45) Date of Patent: Nov. 2, 2004

(54) INTEGRATED CIRCUIT IDENTIFICATION

(75) Inventor: Akira Matsunami, Plano, TX (US)

(73) Assignee: Texas Instruments Incorporated, Dallas, TX (US)

( * ) Notice: Subject to any disclaimer, the term of this patent is extended or adjusted under 35 U.S.C. 154(b) by 0 days.

(21) Appl. No.: 10/309,862

(22) Filed: Dec. 4, 2002

(65) Prior Publication Data

US 2004/0110313 A1 Jun. 10, 2004

(51) Int. Cl.[7] .............................................. G01N 21/86
(52) U.S. Cl. ..................................................... 250/548
(58) Field of Search ............................ 606/10; 250/548

(56) References Cited

U.S. PATENT DOCUMENTS 5,525,808 A * 6/1996 Irie et al. ..................... 250/548
6,482,199 B1 * 11/2002 Neev ............................ 606/10

OTHER PUBLICATIONS

"Nonlaminate Micro Stereolithography Using TFT LCD", T. Hayashi, et al., 1st Euspen Topical Conference on Fabrication and Metrology in Nanotechnology and 2nd General Meeting of the European Society for Precision Engineering and Nanotechnology, May 28–30, 2000, pp. 98–106.
Study on Nonlaminate Micro Stereolithography Using LCD Mask (1st Report)—Nonlaminate Fabrication Using Gray Scale Image, Terrutake Hayashi, et al., Journal of the Japan Society for Precision Engineering, vol. 67, No. 4, pp. 628–632, 2001.

* cited by examiner

Primary Examiner—John F. Niebling
Assistant Examiner—Andre' C. Stevenson
(74) Attorney, Agent, or Firm—Yingsheng Tung; Wade James Brady, III; Frederick J. Telecky, Jr.

(57) ABSTRACT

A method for marking a semiconductor wafer 302 includes the steps of: providing a reticle 300 including liquid crystal pixels; positioning the semiconductor wafer in proximity to the reticle; directing radiation through a first plurality of the pixels onto a first location on the wafer; changing the relative positions of the semiconductor wafer and the reticle; and directing radiation through a second plurality of the pixels onto a second location on the wafer. The first plurality of pixels can be used to form a first mark and the second plurality of pixels can be used to form a second mark, wherein the second mark is different from the first mark. The marks can be made of a pattern of dots in order to save space. The pixels can be selected to form certain marks by using a computer 304 to turn on or off a transistor that may be associated with each pixel. Also described is a system for marking a semiconductor wafer. The system includes a wafer mount 301; a radiation source 306 in proximity to the wafer mount; a reticle 300 which includes liquid crystal pixels and that is positionable between the radiation source and the wafer mount; and a mechanism 303 for changing the relative positions of the reticle and the wafer mount. The radiation source can be non-coherent far-ultraviolet, near-ultraviolet, or visible sources, or a laser.

13 Claims, 4 Drawing Sheets

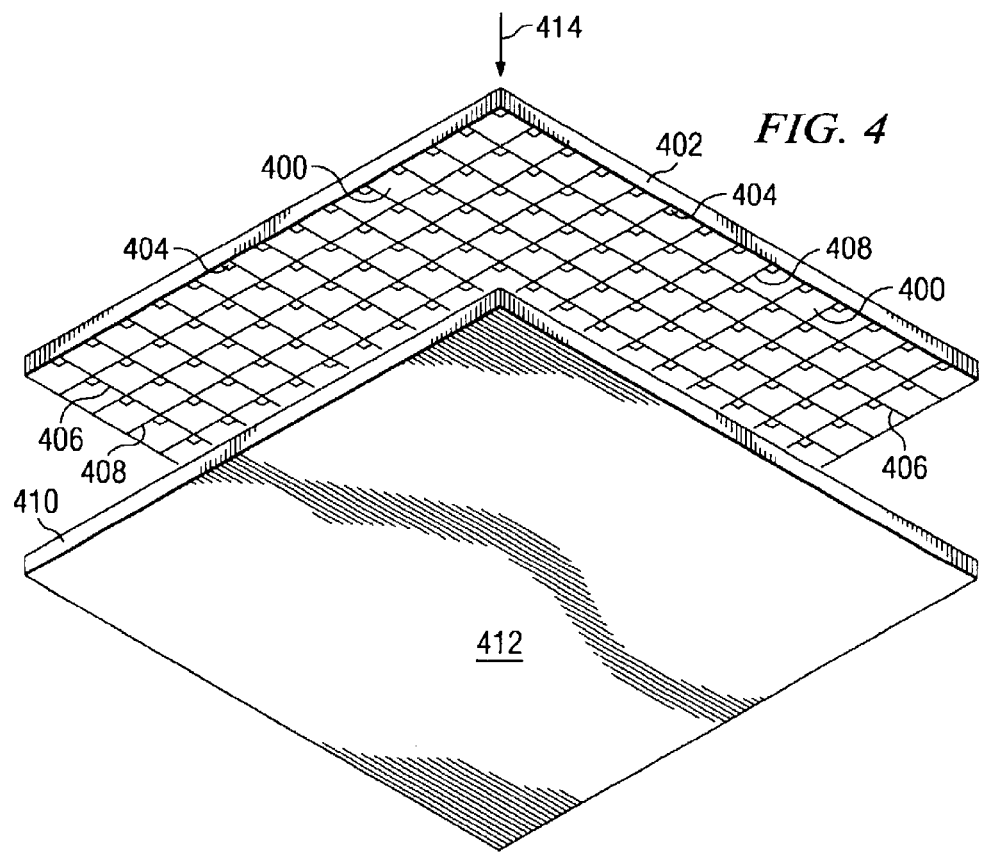
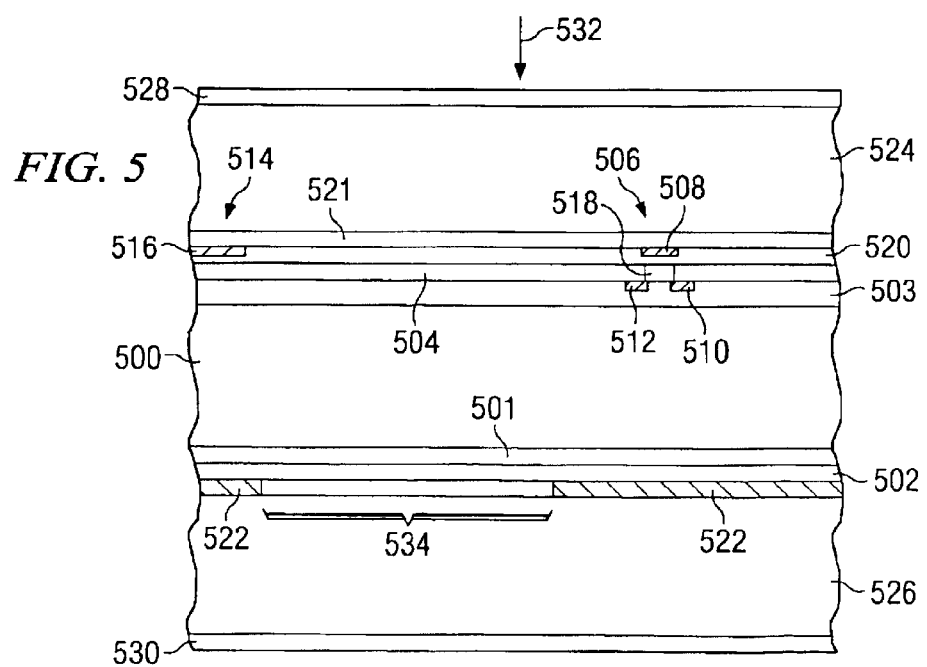

INTEGRATED CIRCUIT IDENTIFICATION

BACKGROUND OF THE INVENTION

This invention is in the field of integrated circuits and in the field of marking integrated circuits for tracking purposes.

There is a need in the semiconductor industry for a reliable method of marking integrated circuit die ("chips") to facilitate tracking of these devices after they are manufactured and sent to customers worldwide. For example, in instances where a customer detects an imperfection in a particular chip, or desires more chips that behave like a particular chip, the ability to ascertain the provenance of the chip and the conditions under which it was fabricated can constitute a competitive advantage for an integrated circuit manufacturer. Whereas, in the past, the marking of the chips on a particular wafer has been possible, it has been possible to only mark chips with a gross level of identification, since all of the chips on a wafer in a given lot of wafers of a particular type of integrated circuit are made with the same set of reticles or masks. Since, for a given level in the fabrication of the chip, that same reticle is stepped across the entire wafer, it has not been possible to give each individual chip its own identifying mark during the wafer fabrication process, where it is most cost efficient to do so. Thus, a problem with a particular chip can only also be traced back as far as the level of identification on the chip allows.

In addition, the continuing demand for smaller chips has put space at a premium and has complicated the task of marking. Typically, all of the wafers in a lot bear the same mark, indicating the device design type, year and month of manufacture, and perhaps the location of manufacture. The identifying mark is also typically large enough to be visually identified with a microscope, for example. As the demand for smaller chips is increasing, the space available for placing such information on each chip has diminished accordingly. For example, for a 1.5 mm×1.5 mm device package, it is not unusual to have space sufficient on the chip for only about five identifying characters, three for the device type and two for the year and month of manufacture, for example. A defect in such a device can only be traced to the year and month in which the chip was made. In many cases, a manufacturer may have fabrication facilities all over the world and many thousands of wafers produced by each of those facilities a month, so much more detailed marking of such small chips is needed. It is clear that there is a need in the industry for better ways of marking integrated circuit die.

BRIEF SUMMARY OF THE INVENTION

One embodiment of the invention is a method for marking a semiconductor wafer. The method includes the steps of: providing a reticle including liquid crystal pixels; positioning the semiconductor wafer in proximity to the reticle; directing radiation through a first plurality of the pixels onto a first location on the wafer; changing the relative positions of the semiconductor wafer and the reticle; and directing radiation through a second plurality of the pixels onto a second location on the wafer. The first plurality of pixels can be used to form a first mark and the second plurality of pixels can be used to form a second mark, wherein the second mark is different from the first mark. The marks can be made of a pattern of dots in order to save space. The pixels can be selected to form certain marks by using a computer to turn on or off a transistor that may be associated with each pixel.

Another embodiment is a system for marking a semiconductor wafer. The system includes a wafer mount; a radiation source in proximity to the wafer mount; a reticle which includes liquid crystal pixels and that is positionable between the radiation source and the wafer mount; and a mechanism for changing the relative positions of the reticle and the wafer mount. The radiation source can be non-coherent far-ultraviolet, near-ultraviolet, or visible sources, or a laser.

Still another embodiment of the invention includes a method for marking a semiconductor wafer. The method includes the step of providing a test probe tool. The tool includes a wafer chuck, a test head in proximity to the wafer chuck, a probe card attached to the test head, and a laser mounted on the tool. The method also includes the steps of mounting a semiconductor wafer on the wafer chuck; contacting a first location on the wafer with the probe card; making a first mark on the first location with the laser; changing the relative positions of the probe card and the wafer; contacting a second location on the wafer with the probe card; and making a second mark on the second location with the laser. The second mark is different from the first mark, and may include a pattern of dots that indicate the first and second locations on the wafer. The steps of contacting a first location on the wafer and making a first mark on the first location may be performed concurrently.

An advantage of the invention is that it allows for a chip-level custom identification mark for each chip on a wafer.

BRIEF DESCRIPTION OF THE SEVERAL VIEWS OF THE DRAWINGS

The invention can be more fully understood by reading the following detailed description of preferred embodiments of the invention with reference to the accompanying drawings. One skilled in the art will appreciate that the drawings are not to scale; in particular, the vertical dimension is typically exaggerated to better show the details of the embodiments.

FIG. 4 is a detailed perspective view of the LCD mask shown in FIG. 3 illustrating pixels in the mask.

FIG. 5 is a detailed cross-sectional view of one of the pixels shown in FIG. 4.

DETAILED DESCRIPTION OF THE INVENTION

Figure 1A:
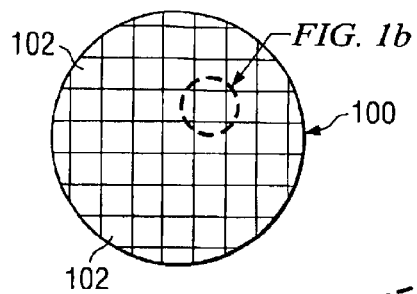
FIG. 1a is a plan view of a semiconductor wafer showing the division of the wafer surface into chips.
Figure 1B:
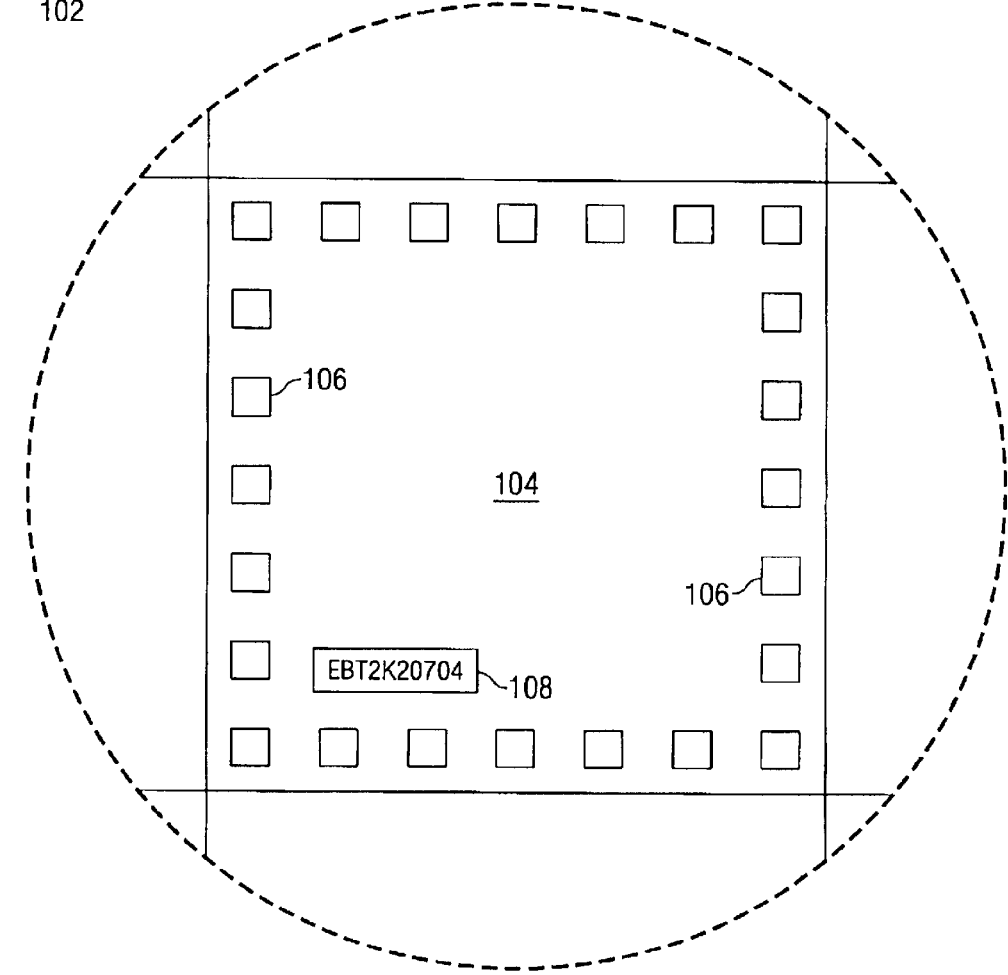
FIG. 1b is a plan view of a chip.
Figure 2A:
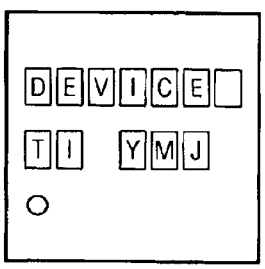
FIG. 2a is an example of marking on a 4 mm×4 mm chip.
Figure 2B:
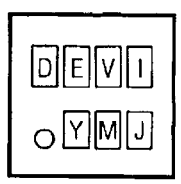
FIG. 2b is an example of marking on a 2 mm×2 mm chip.
Figure 2C:
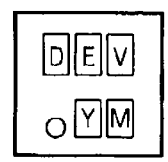
FIG. 2c is an example of marking on a 1.5 mm×1.5 mm chip.

FIG. 1a shows a plan view of a wafer 100 segmented into individual dice or chips 102. FIG. 1b shows detail of a particular chip 104, including bond pads 106, and an identifying mark 108. Ideally, the mark would contain information indicating the facility in which the chip was made, the day, month, and year on which it was made, the lot of wafers with which it was processed, as well as the number of the wafer in that lot, and, finally, the location the particular die occupies upon the wafer. Such a mark may appear as follows: "EBT2K20704-MIB-02-17," where "EBT" is the fabrication facility, "2K2" is 2002, the year of fabrication, "07" is July, the month of fabrication, "04" is the fourth day of July, "MIB" is the lot identifier, "02" is the wafer number within the lot, and "17" is the die location on the wafer. Of course, a manufacturer ID also appears at some location on the chip. Putting this much information on a chip in a conventional size and lettering format can consume too much space. Consequently, in the past, the information has been truncated in accordance with the space available for a given chip design. FIG. 2a, for example, shows how the information can appear on a chip in a 4.0 mm×4.0 mm package. In this case the device information is allocated seven blocks, the manufacturer identification consumes two blocks, and the year, month, and facility of the fabrication consume the remaining three blocks. On a chip in a 2.0 mm×2.0 mm package, the information is truncated further, as shown in FIG. 2b, and even further for a chip in a 1.5 mm×1.5 mm package as shown in FIG. 2c.

One embodiment of the invention is a method for forming a lot identification mark, including a chip-specific identifier. In step-and-repeat lithography, the same set of reticles is used to form each of the chips on a wafer, and each of the wafers in a lot. Using conventional reticles, a custom identification mark for each wafer would require at least one custom reticle for each wafer in a lot, most likely a custom reticle for the uppermost metal layer, or perhaps a reticle used to pattern an upper dielectric layer. Similarly, a custom identification mark for each chip on a wafer would require a custom reticle for each chip or group of chips patterned with that particular reticle. Both of these approaches are impractical with conventional reticle technology because of the expense and complication involved in manufacturing and using so many custom reticles. The inventive concepts described here are a solution to those limitations.

Figure 3:
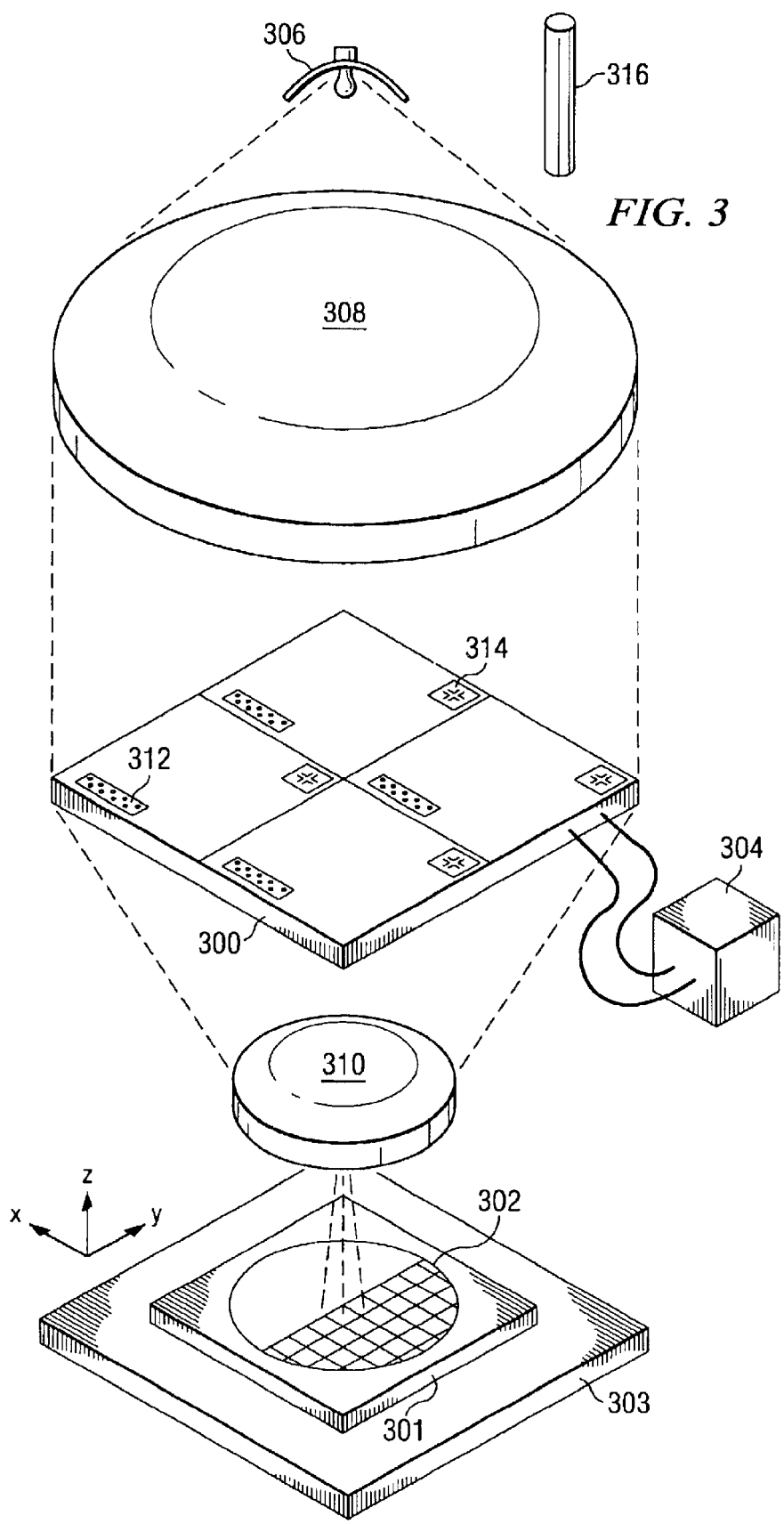
FIG. 3 is a photolithographic apparatus incorporating an LCD mask.

FIG. 3 is a conceptual diagram of an embodiment marking system including a liquid crystal display (LCD) reticle or mask 300 that can be electronically customized for each step as the reticle is stepped across the surface of wafer 302. The customization of the LCD reticle can be accomplished by selectively turning on transistors associated with individual LCD pixels through commands from a computer 304, such as the computer used by the stepper for automatic pattern recognition, alignment, and so forth. The LCD reticle 300 can be adapted to fit into the mechanism (not shown) used to hold a conventional reticle, in which case the deep-UV radiation source 306 used for the other photolithographic steps in the process can be used for chip marking with the LCD reticle 300. A laser could alternatively be used as the radiation source 306. The system includes a lens 308 for collimating the radiation from source 306, as well as optics 310 for reducing the images on the LCD reticle 300 as they are projected onto the surface of wafer 302 (e.g. a 10:1 reduction). The LCD reticle 300 includes pixels that can be turned on or off at the command of computer 304 to form identifying marks at the desired locations within the reticle. The LCD reticle can have pixels distributed across the entirety of its surface, or in select locations, which may be preferable where the identifying mark appears in a dedicated space for each of the chip designs made using the photolithographic tool. In the preferred embodiment, however, the pixels cover the reticle so that a completely custom mark may be made at any point within the reticle. This allows the same LCD reticle to be used for virtually any chip design fabricated using the photolithographic tool, a feature that a custom fabrication facility would find valuable, for example. The LCD reticle 300 also includes alignment marks 314 at locations on the reticle that correspond to alignment marks on other reticles in the reticle set used to manufacture a chip. The alignment marks 314 may be permanent features on the glass or quartz surface of the LCD mask, or they may be formed using LCD pixels in a manner similar to the way in which the identifying marks 312 are formed, i.e. completely customizable in terms of size, shape, and location within the reticle 300. The tool incorporates alignment optics 316 as well as precision stepping machinery 303 for moving the wafer mount 301 relative to the reticle 300 in x, y, and z directions as the reticle is used to make exposures across the surface of wafer 302.

In an alternative embodiment, rather than an LCD reticle, an entire LCD mask could be used to form completely custom identifying marks on every chip on the wafer in a single lithographic step. Reducing optics and the simplified marking system described below facilitate such a wafer-scale mask. In another embodiment, the LCD reticle can be stepped across the wafer using a separate tool (rather than the tool used in the photolithographic steps performed to create the integrated circuits on the wafer), in which case a laser or a longer wavelength radiation source may be more easily used, including near-UV and visible light (such as the light available from the illuminator of a camera's auto focus system, for example).

FIG. 4 is a perspective view showing LCD pixels 400 arranged on an inside face of a quartz or glass substrate 402. The pixels are on the order of 10 to 30 μm square and are arranged in a densely packed grid. Associated with each pixel 400 is a silicon transistor 404 used to control operation of the pixel. The transistor is coupled to one of a plurality of gate lines 406 and drain lines 408 which are orthogonally arranged on the substrate between pixels. A space or gap separates the top substrate 402 from the bottom quartz or glass substrate 410. The gap between the two substrates is filled with liquid crystal polymer (not shown). The top or outside surface of substrate 402 is covered with a polarizing film (not shown), and the bottom or outside surface of substrate 410 is also covered with a polarizing film 412. The polarizing films are arranged such that their polarizing angles are orthogonal to one another, for reasons described further below. Arrow 414 indicates the direction from which light impinges upon the reticle.

FIG. 5 is a cross-sectional view of a single pixel in the reticle shown in FIG. 4. The pixel is based around a liquid crystal core 500, which includes rod-like molecules in a cyanobiphenyl compound, for example, about 1 to 5 μm thick. The liquid crystal molecules are aligned with one another throughout the thickness of the layer when a voltage is applied across the layer. Hence, in this biased state, polarized light passing through the layer is unaltered, and upon encountering an orthogonally arranged polarizer at the opposite side of the layer, is completely blocked from passing through. In contrast, in the absence of an applied voltage, the molecules at various points throughout the thickness of the layer are twisted relative to one another such that polarized light entering the layer is rotated as it passes through the layer. Proper selection of the liquid crystal results in light twisted at right angles to the entering light such that it passes through the orthogonally arranged polarizer at the opposite side of the layer. This is the principle through which an LCD pixel can perform the functions of a light valve or optical switch. A reticle comprising millions of these pixels has the resolution necessary for forming completely customizable marks of indicia on a semiconductor wafer by simply turning on or off selected ones or groups of pixels.

The voltage potential is applied across liquid crystal 500 using transparent electrodes made of indium-tin oxide (ITO) for example. In FIG. 5, common electrode 502 completely covers the bottom of the liquid crystal layer 500. Note that ITO film 502 is separated from the liquid crystal in this embodiment by an orientation film 501, which is polyimide for example. Similarly, on the opposite side of the liquid crystal layer 500, another polyimide orientation layer 503 separates the liquid crystal layer 500 from ITO electrode 504. Electrode 504 is not continuous, but is instead divided into pixel sized patches as shown in FIG. 4. Thus, the voltage potential across the section of liquid crystal shown in FIG. 5 is applied between the pixel-sized patch electrode 504 and the common electrode 502. The remaining elements of the structure of FIG. 5 include silicon transistor 506, including a gate terminal 508, drain terminal 510, and source terminal 512 (all of aluminum for example). As mentioned above with respect to FIG. 4, the gate and drain terminals are connected to lines (not shown) that extend to the edges of the pixel array, and are the means through which the pixel is controlled. The source terminal 512 is connected to pixel electrode 504, which also forms the top plate of a capacitor 514 formed between pixel electrode 504 and an aluminum bottom plate 516. Capacitor 514, one of which is associated with each pixel, improves the uniformity of the transmitted image across the reticle. The channel of transistor 506 is formed in amorphous or polycrystalline silicon 518. Silicon nitride layer 520 serves as both the gate dielectric and the dielectric layer for capacitor 512. On the opposite side of the liquid crystal layer 500, a shield 522 (of aluminum for example) helps prevent the passage of stray or reflected light through the pixel and increases the pixel contrast. All of the aforementioned structure is sandwiched between two quartz substrates, a top substrate 524 and a bottom substrate 526. Quartz is preferable to glass because of its better optical properties and ability to withstand the relatively high temperatures used in forming the transistors, for example. The top or outer surface of top substrate 524 is covered with a polarizing film 528 and the bottom or outer surface of bottom substrate 526 is covered with a polarizing film 530 arranged to have an orthogonal polarizing angle to that of film 528.

In operation, light impinging on the pixel from the direction 532 passes through polarizing film 528, through quartz substrate 524, through silicon oxide layer 521, through silicon nitride layer 520, through pixel electrode 504, through polyimide layer 503, where it reaches the liquid crystal layer 500. The behavior of the light as it passes through the liquid crystal is dependent upon whether a potential exists between electrode 504 and common electrode 502. If the voltages applied to the drain 510 and gate 508 electrodes are digital "highs", a potential is formed between the electrodes, and the liquid crystal molecules align with the potential and therefore do not alter the light as it passes through the crystal. If the gate voltage is a digital "low", no potential exists across the electrodes, and the liquid crystal molecules exist in their progressively rotated state such that the polarized light is rotated as it passes through layer 500. Whether rotated or not, the light then passes through the polyimide orientation layer 501, through common electrode 502, and through aperture 534 formed in shield layer 522, and then through quartz substrate 526. At this point, if the light has passed unaltered through layer 500, it will be prevented from passing through the orthogonally-arranged polarizing film 530 (i.e. the pixel is "off"). In contrast, if the light was rotated as it passed through layer 500, it will pass through polarizing film 530 (i.e. the pixel is "on") where it can proceed to impinge upon a photoresist layer on the wafer surface, for example.

Figures 6, 7:
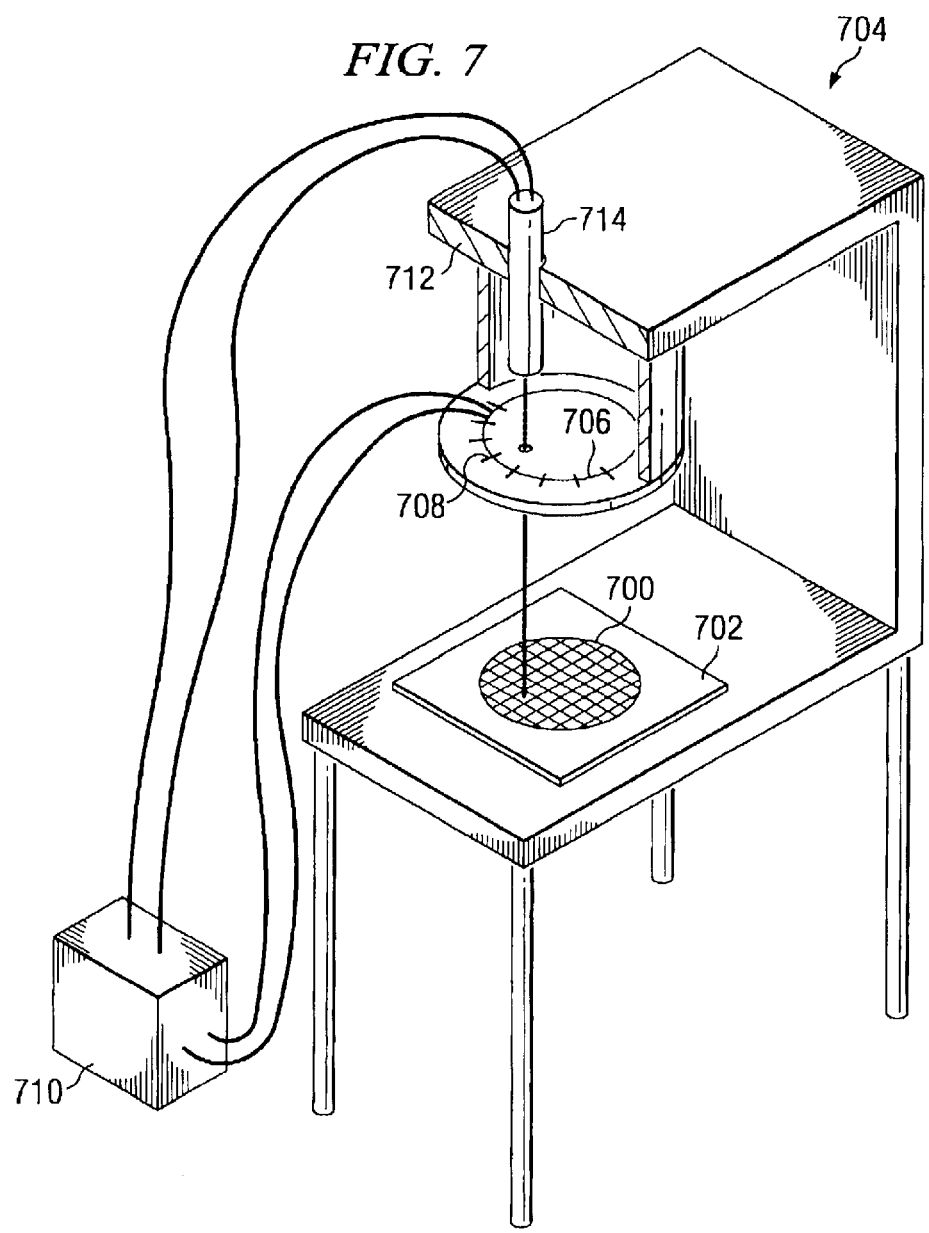
FIG. 6 is the prior art dot-based Braille coding system.
FIG. 7 is a probe test tool incorporating a marking laser.

Use of an LCD reticle is made more practical by employing reducing optics commonly used in a projection lithography system to make the image projected onto the wafer smaller than the images on the LCD reticle. In addition, the shapes used in marking the identity of a chip or wafer can be simplified to accommodate the lower resolution of a LCD reticle as compared to a conventional reticle. For example, rather using roman characters and arabic numerals (as shown in FIGS. 2a to 2c), the mark could be made using a code of dots or similar marks, such as is used in the Braille system for the vision-impaired. FIG. 6 shows how the numbers 0–9 are formed in the Braille system. The fact that the code in this embodiment can be conveyed with a very simple feature such as a dot is important in view of the limited resolution that can be accomplished with a mask comprising a liquid crystal display. Distortion that can result from factors such poor transmission of light or UV radiation through the reticle, as well as from lateral development, standing waves, reflection, and so forth that make conventional lithography so challenging, is much less of an issue if the goal is simply to form a pattern of dots. A system of four dots can represent fifteen distinct characters, which is sufficient for the purposes of chip identification.

In another embodiment of the invention, the invariant portion of the identification mark is formed in the traditional manner, but the variable information containing lot information, wafer identification, and chip number is formed with the LCD reticle using the dot code. This has the advantage of allowing a customer without knowledge of the code to discern certain information about the die including the device number, for example, while still allowing the manufacturer the ability to obtain the full set of information contained in the dot code.

In an alternative embodiment, a laser is used to directly write the mark on the wafer surface at a convenient point in the process. An example is at the wafer probe test step, in which the wafers are tested in their final form prior to dicing and packaging. In FIG. 7, a wafer 700 is mounted on the chuck 702 of a wafer probe tester 704. A probe card 706 containing probes 708 coupled to computer 710 is supported by test head 712, which can be lowered to put probes 708 into contact with the wafer 700. Mounted on the test head 712 is a laser 714 which can be controlled by computer 710 (or by a separate electronic control means) to form an identifying mark in an upper metal or dielectric layer on each chip on wafer 700 as the probe card 706 is moved from chip to chip across the wafer. In this way, the marking operation can be integrated into the probe step without adding additional process time. Laser 714 is controlled to perform its "writing" function by precision alignment and movement mechanisms. In an alternative embodiment, the laser can be incorporated into a tool separate from the tester for increased flexibility. Also, as described above, the laser can be used in conjunction with an LCD mask to form customer identification marks at the chip or wafer level.

While the present invention has been described according to its preferred embodiments, it is of course contemplated that modifications of, and alternatives to, these embodiments, such modifications and alternatives obtaining the advantages and benefits of this invention, will be apparent to those of ordinary skill in the art having reference to this specification and its drawings. It is contemplated that such modifications and alternatives are within the scope of this invention as claimed hereinbelow.

I claim:

1. A method for marking a semiconductor wafer, comprising the steps of:
   providing a reticle comprising liquid crystal pixels;
   positioning said semiconductor wafer in proximity to said reticle;
   directing radiation through a first plurality of said pixels onto a first location on said wafer;
   changing the relative positions of said semiconductor wafer and said reticle; and
   directing radiation through a second plurality of said pixels onto a second location on said wafer.

2. The method of claim 1, wherein said step of directing radiation through a first plurality of said pixels comprises the step of forming a first mark on said first location of said wafer; and wherein said step of directing radiation through a second plurality of said pixels comprises the step of forming a second mark on said second location of said wafer; wherein said second mark is different from said first mark.

3. The method of claim 1, wherein said steps of directing radiation through said first and second pluralities of said pixels further comprises forming patterns of dots on said wafer.

4. The method of claim 1, wherein said step of providing a reticle comprising liquid crystal pixels further comprises providing a reticle comprising a transistor associated with each of said pixels.

5. The method of claim 4, wherein said step of providing a reticle comprising liquid crystal pixels further comprises the step of providing a computer coupled to each said transistor associated with each of said pixels.

6. The method of claim 5, wherein said steps of directing radiation through first and second pluralities of pixels further comprises the step of using said computer to select said first and second pluralities of pixels.

7. The method of claim 1, further comprising the step of positioning a reducing lens between said reticle and said wafer such that said radiation passes through said reducing lens before reaching said wafer.

8. A method for marking a semiconductor wafer, comprising the steps of:
   providing a test probe tool, said tool comprising a wafer chuck, a test head in proximity to said wafer chuck, and a probe card attached to said test head, said test probe tool further comprising a laser mounted on said tool;
   mounting a semiconductor wafer on said wafer chuck;
   contacting a first location on said wafer with said probe card;
   making a first mark on said first location with said laser;
   changing the relative positions of said probe card and said wafer;
   contacting a second location on said wafer with said probe card;
   making a second mark on said second location with said laser; said second mark different from said first mark.

9. The method of claim 8, wherein said steps of making said first and second marks comprise forming first and second patterns of dots at said first and second locations on said wafer.

10. The method of claim 9, wherein said step of forming first and second patterns of dots comprises forming patterns of dots that indicate the positions of said first and second locations on said wafer.

11. The method of claim 9, wherein said steps of making said first and second marks comprise forming first and second sets of letters and numerals at said first and second locations on said wafer.

12. The method of claim 11, wherein said step of forming said first and second sets of letters and numerals comprises forming sets of letters and numerals that indicate the positions of said first and second locations on said wafer.

13. The method of claim 8, wherein said steps of contacting a first location on said wafer and making a first mark on said first location are performed concurrently.

* * * * *